United States Patent [19]

Owada et al.

[11] Patent Number: 5,160,665

[45] Date of Patent: Nov. 3, 1992

[54] AEROSOL COMPOSITION EXHIBITING CRACKLING SOUND USING ALIPHATIC HYDROCARBON PROPELLANTS

[75] Inventors: Ryoichi Owada, Yawata; Satoshi Mekata, Hirakata; Kunio Ohguri, Kasukabe, all of Japan

[73] Assignee: Osaka Aerosol Industries Corporation, Osaka, Japan

[21] Appl. No.: 453,887

[22] Filed: Dec. 20, 1989

[30] Foreign Application Priority Data

Dec. 27, 1988 [JP] Japan .................................. 1-334975
May 25, 1989 [JP] Japan .................................. 2-134028

[51] Int. Cl.$^5$ ........................ B01J 13/00; A61K 9/12
[52] U.S. Cl. ..................................... 252/307; 252/90; 424/45; 424/47
[58] Field of Search .................. 252/305, 307, 90; 424/45, 47, DIG. 1

[56] References Cited

U.S. PATENT DOCUMENTS

| | | | |
|---|---|---|---|
| 2,524,590 | 10/1950 | Boe | 252/305 |
| 3,103,468 | 9/1963 | Shepard et al. | 167/87.1 |
| 3,161,460 | 12/1964 | Huber | 8/142 |
| 3,211,563 | 10/1965 | Reed | 106/213 |
| 3,639,568 | 2/1972 | Schmitt | 252/305 X |
| 3,728,276 | 4/1973 | Lieberman et al. | 252/305 |
| 3,787,566 | 1/1974 | Gauvreau | 424/45 |
| 3,947,568 | 3/1976 | Bates et al. | 424/47 |
| 4,574,052 | 3/1986 | Gupte et al. | 252/90 |

OTHER PUBLICATIONS

Paul A. Sanders, "Unusual Aqueous Aerosol Foams", American Perfumer and Cosmetics, vol. 48, Oct. (1969).

Primary Examiner—Robert L. Stoll
Assistant Examiner—Daniel S. Metzmaier
Attorney, Agent, or Firm—Armstrong & Kubovcik

[57] ABSTRACT

An aerosol composition which forms a foam exhibiting a cracking sound upon defoaming when subjected to blow out in the form of a mist or a foam, containing an aliphatic hydrocarbon having a boiling point of $-5°$ to $+40°$ C. The aerosol composition of the present invention has the advantages that a uniform dispersion can be easily formed with using various effective components, that it has an improved fast-drying property and produces an increased foam crackling sound and that it does not affect the environment adversely.

5 Claims, No Drawings

AEROSOL COMPOSITION EXHIBITING CRACKLING SOUND USING ALIPHATIC HYDROCARBON PROPELLANTS

BACKGROUND OF THE INVENTION

The present invention relates to an aerosol composition, and more particularly to an aerosol type foam composition which upon release of pressure therefrom forms a foam which exhibits a crackling sound when subjected to blow out in the form of a mist or a foam.

Conventional aerosol products include a class of products such as hair sprays with which an effective ingredient is blown out in the form of a mist and those such as shaving creams with which an effective ingredient is ejected as a foam. Recently, as described in Japanese Examined Patent Publication No. 32053/1970, Japanese Unexamined Patent Publication No. 54784/1987, and the like, there have been developed aerosol compositions for the production of a foam which exhibits a crackling sound when the foam delivered from an aerosol container is subjected to shear on the user's palms upon applying to the skin.

However, the aerosol composition for the production of a foam disclosed in Japanese Examined Patent Publication No. 32053/1970 is of the type that a water-insoluble oil fraction contained in cosmetically active ingredients and water have to be shaken to give an emulsion. When the product is not used for a long period of time, there occurs a separation of the aqueous and oil phases, so that intense and/or prolonged shaking is required to obtain a uniform dispersion in every use. Moreover, a large quantity of water must be used and, consequently, when the foam is applied to the skin by hand, drying of the foam is delayed.

The composition disclosed in Japanese Unexamined Patent Publication No. 54784/1987 has advantages that water-insoluble oily ingredients are easily and uniformly dispersed into aqueous ingredients and the foam formed from the composition is dried in a short time. However, the composition has some disadvantages such that the cost is expensive and environmental deterioration might be induced as well as the composition disclosed in Japanese Examined Patent Publication No. 32053/1970 has because chlorofluorocarbon is employed as a main component of the propellant.

It is an object of the present invention to provide a novel aerosol composition of which water-insoluble oily ingredients are easily and uniformly dispersed into aqueous ingredients.

A further object of the present invention is to provide an aerosol composition comprising ingredients which would not deteriorate the environment and which is excellent in fast-drying property.

A still further object of the present invention is to provide an aerosol composition which upon release of pressure therefrom forms a foam which exhibits a cracking sound when subjected to blow out in the form of a mist or a foam.

These and other objects of the present invention will become apparent from the description hereinafter.

SUMMARY OF THE INVENTION

In accordance with the present invention, there is provided an aerosol composition which forms a foam exhibiting a crackling sound upon defoaming when subjected to blow out in the form of a mist or a foam, containing an aliphatic hydrocarbon having a boiling point of $-5°$ to $+40°$ C.

DETAILED DESCRIPTION

The aerosol composition of the present invention is characterized in that an aliphatic hydrocarbon having a boiling point of $-5°$ to $+40°$ C. is contained in the composition. The aerosol composition is mainly composed of a concentrate and a propellant.

The aliphatic hydrocarbon having a boiling point of $-5°$ to $+40°$ C. is used not only as a propellant to form a suitable foam which exhibits a crackling sound generated upon defoaming when the composition is released from an aerosol container but also as an ingredient to impart a fast-drying property, which is effective for drying of a formed foam, to the composition.

Accordingly, when the aliphatic hydrocarbon having a boiling point of $-5°$ to $+40°$ C. is used, the following novel results unexpectable from prior art can be obtained.

(1) Athough a conventional propellant such as chlorofluorocarbon is alleged to destroy the environment, the aliphatic hydrocarbon having a boiling point of $-5°$ to $+40°$ C. used as a propellant would not affect the environment.

(2) The aerosol composition in which the aliphatic hydrocarbon having a boiling point of $-5°$ to $+40°$ C. is used is superior in a crackling sound generated upon defoaming to that in which propane or isobutane is used as a propellant.

(3) There is no necessity to use a conventional ingredient to impart a fast-drying property because the aliphatic hydrocarbon having a boiling point of $-5°$ to $+40°$ C. acts as an ingredient to impart a fast-drying property.

(4) Accordingly, when the aerosol composition of the present invention is prepared, there is no necessity to employ a conventional complex process for preparing the composition in which a propellant and an ingredient to impart a fast-drying property should be used at a time, and the cost for the ingredient to impart a fast-drying property can be cancelled.

It is disclosed in Japanese Patent Examined Publication No. 34912/1974 that n-pentane is used as a post-foaming agent for a post-foaming gel loaded in an aerosol container of double compartment construction in an amount of about 5% by weight of the ingredients contained in the aerosol container. However, the ingredients are released not in the form of a mist or a foam but in the form of a gel, and the gel when released from the container would neither exhibit a crackling sound nor show fast-drying property. Accordingly, from the description of the above document, the aerosol composition of the present invention could not be found or expected at all.

On the other hand, since a specific aliphatic hydrocarbon having a boiling point of $-5°$ to $+40°$ C. is employed in the aerosol composition of the present invention, the conditions of the aerosol composition in an aerosol container and a formed foam are stable, and the formed foam is colorless and optically imparts refreshment. In particular, when pentane is contained in the aerosol composition of the present invention, a formed foam is excellent in transparency.

Examples of the aliphatic hydrocarbon having a boiling point of $-5°$ to $+40°$ C. are, for instance, pentane, n-butane (boiling point: $-0.5°$ C.), and the like. Examples of the pentane are, for instance, i-pentane (boiling point: 27.9° C.), n-pentane (boiling point: 36.1° C.), neopentane (boiling point: 9.5° C.), and the like. The above aliphatic hydrocarbons can be used alone or in admixture thereof. Among them, i-pentane and n-butane are preferable from the viewpoint of safety for human bodies as i-pentane is registered in Japan Cosmetic Ingredients Dictionary and n-butane is registered in the Standards of Raw Materials for Cosmetics.

The pentane is contained as a main component of a propellant, and can also be contained as an effective ingredient as occasion demands.

In the propellant, pentane acts as a pressure control agent having an excellent characteristic to form a suitable foam which exhibits a crackling sound when the aerosol composition is delivered from an aerosol container. When there is a problem in dispersibility of the concentrate and the propellant of which main component is pentane, the concentrate can be uniformly dispersed with the propellant by beforehand dispersing pentane uniformly in the concentrate.

The total amount of pentane contained in the concentrate and the aliphatic hydrocarbon having a boiling point of $-5°$ to $+40°$ C. contained in the propellant is adjusted to 10 to 90 parts by weight (hereinafter referred to as "parts"), preferably 15 to 85 parts, in particular 20 to 80 parts based upon 100 parts of the aerosol composition. When the total amount is less than 10 parts, there is a tendency to delay the defoaming and to disappear a crackling sound at defoaming. When the total amount is more than 90 parts, there is a tendency that the effective ingredients do not uniformly disperse in the concentrate and the aliphatic hydrocarbon having a boiling point of $-5°$ to $40°$ C. since the amount of the effective ingredients is too little.

When pentane is solely used as a propellant, the aerosol composition would not be sufficiently delivered from an aerosol container because the vapor pressure of the propellant is too low. Accordingly, it is preferable that pentane is partly replaced by a liquefied gas such as i-butane, n-butane, propane, dimethyl ether, dichlorodifluoromethane, dichlorotetrafluoroethane, monochlorodifluoromethane, monochlorodifluoroethane or tetrafluoroethane, or a compressed gas such as $N_2$, $CO_2$ or $N_2O$. Among them, i-butane and and n-butane are particularly preferable because they would not adversely affect the environment and a foam exhibiting a crackling sound is favorably formed when the composition delivered from an aerosol container in the form of a mist or a foam.

The amount of the propellant other than pentane cannot be absolutely determined because the proportion of pentane to the other propellant should be changed depending on the kind of such other propellant. However, it is preferable to maintain the amount of such propellant other than pentane within 5 to 95% by weight, more preferably within 10 to 90% by weight, in particular within 20 to 80% by weight of the amount of pentane. When the amount of the propellant other than pentane is less than 5 % by weight, there is a tendency that the aerosol composition cannot be effectively delivered from an aerosol container because the vapor pressure in the aerosol container is too low. When the amount of the propellant other than pentane is more than 95% by weight, there is a tendency that the vapor pressure in the aerosol container is too high. As a propellant, 100% by weight of n-butane, that is, n-butane solely can be used without any problem.

When compressed gas is used as a propellant, it is preferable that the vapor pressure in the aerosol container is not more than 8 $kg/cm^2$ at $+35°$ C.

The concentrate used in the aerosol composition of the present invention is mainly composed of effective ingredients as primary components and secondary components such as pentane, alcohol component, surface active agents, powder, and purified water to be optionally employed as occasion demands.

Examples of the alcohol component are, for instance, alcohols such as ethanol and isopropyl alcohol. Since the alcohol component is capable of dissolving both water-soluble compounds and various organic compounds insoluble in water, the alcohol component is used as a solubilizing agent or a dispersing agent. Moreover, since ethanol and isopropyl alcohol have a low boiling point and easily vaporize, they are also useful as an agent to meet the fast-drying requirement or to give a refreshing sensation to the user. In addition, both of ethanol and isopropyl alcohol have excellent defoaming properties and are useful as a component for obtaining a distinctive crackling sound.

The alcohol component is usually used in the form of aqueous solution. The concentration of the aqueous alcohol solution is preferably adjusted to at most 60% by weight, more preferably 5 to 40% by weight, in particular 5 to 30% by weight. When the concentration of the aqueous alcohol solution is less than 3% by weight, in particular when pentane is contained in the concentrate, there is a tendency that a water-insoluble oily effective component is hardly dispersible in the uniform state with the aqueous fraction and the product becomes slow-drying. Accordingly, it is preferable that the concentration is at least 3% by weight. On the other hand, when the alcohol concentration exceeds 60 % by weight, there is a tendency that the compatibility with an aliphatic hydrocarbon having a boiling point of $-5°$ to $+40°$ C. will be too good. Thus, foaming becomes poor and the aerosol composition does not exhibit a crackling sound.

The aqueous alcohol solution is used in an amount of at most 60% by weight, preferably at most 50% by weight, more preferably at most 40% by weight, in particular 35% by weight of the aerosol composition. When the amount is more than 60% by weight of the aerosol composition, there is a tendency that the destruction of the foam is delayed or the crackling sound is not given. In order to achieve a uniform dispersion of the alcohol component and water-insoluble oily effective ingredients although pentane is not contained in the concentrate, or to improve the dispersibility of the components of the aerosol composition, it is desirable that the aqueous alcohol solution is used in an amount of at least 2% by weight, preferably at least 5% by weight, more preferably at least 10% by weight, in particular at least 12% by weight of the concentrate.

The surface active agent is used to ensure a uniform dispersion of both the concentrate and a propellant of which main component is an aliphatic hydrocarbon having a boiling point of $-5°$ to $+40°$ C., and both the concentrate in which pentane is contained and a propellant. Examples of the surface active agent are, for instance, anionic surface active agents such as carboxylic acid salts, sulfuric acid salts and sulfonic acid ester salts; cationic surface active agents such as alkylamine salts, alkyl quarternary ammonium salts, benzalkonium salts, benzethonium chlorides, pyridinium salts, imidazolinium salts; nonionic surface active agents such as polyoxyethylene alkyl ethers, polyoxyethylene-polyoxypropylene alkyl ethers, homogeneous polyoxyethylene alkyl ethers, polyoxyethylene sec-alcohol ethers, polyoxyethylene alkylphenyl ethers, polyoxyethylene sterolethers, polyoxyethylene lanolin derivatives, polyoxyethylene-polyoxypropylene block copolymers, polyoxyethylene-polyoxypropylene alkyl ethers, polyoxyethylene glycerine fatty acid esters, polyoxyethylene castor oils and hydrogenated castor oils, polyoxyethylene sorbitan fatty acid esters, polyoxyethylene sorbitol fatty acid esters; and the like. Other surface active agents which are able to help ensure the above-mentioned uniform dispersion can likewise be employed. Among the above surface active agents, nonionic surface active agents are particularly preferably used from the viewpoint of corrosion resistance of a commercial metal container for the aerosol composition.

It is preferable that the amount of the surface active agent is adjusted so that the surface active agent is contained in an amount of 0.03 to 5% by weight, preferably 0.05 to 4% by weight, in particular 0.1 to 3% by weight in the aerosol composition. When the amount is less than 0.03% by weight, intense shaking or prolonged shaking is necessitated in order to achieve a uniform dispersion of both the concentrate and a propellant of which main component is an aliphatic hydrocarbon having a boiling point of $-5°$ to $+40°$ C. and both the concentrate containing pentane and a propellant. On the other hand, when the amount of the surface active agent exceeds 5% by weight, , there is a tendency that the foam produced from the aerosol composition becomes sticky and the stickiness may give an uncomfortable sensation.

A powder can be used as an excipient. The powder may be virtually any kinds of particulate materials that are insoluble in the aerosol composition of the present invention. Examples of the powder are, for instance, magnesium oxide, zinc oxide, titanium dioxide, precipitated calcium carbonate, heavy magnesium carbonate, light magnesium carbonate, heavy calcium carbonate, yellow iron oxide, red iron oxide, black iron oxide, ultramarine, chromium oxide, silicic acid anhydride, magnesium silicate, talc, kaolin, bentonite, mica, titanium mica, bismuth oxychloride, zirconium dioxide, chromium hydroxide, calamine, Nylon powder, polyethylene powder, polystyrene powder, acrylic resin powder, cellulose powder, a hybrid fine powder composed of an inorganic pigment such as titanium dioxide and an organic polymer powder such as a composite material composed of Nylon 12, and the like. These powders can be used alone or in admixture thereof. Among them, talc, titanium dioxide, zinc oxide, precipitated calcium carbonate, heavy calcium carbonate, light magnesium carbonate, heavy magnesium carbonate, and the like can be preferably used because it exhibits an effect on the same level as the case of using a surface active agent when an emulsion is prepared by shaking the aqueous fraction and the oil fraction together or increases the effect which is given by using a surface active agent and in certain cases an emulsion can be prepared by shaking the aqueous fraction with the oil fraction gently without employing a surface active agent. It is desirable that the size of the powder is adjusted to not more than 100 $\mu$m, more preferably 20 to 50 $\mu$m in order to avoid the clogging in a nozzle of a container for the aerosol composition when the aerosol composition is delivered from the container. It is desirable that the amount of the powder is adjusted to at most 10% by weight, preferably at most 8% by weight, more preferably at most 5% by weight of the aerosol composition. When the amount of the powder exceeds 10% by weight of the aerosol composition, stains may remain on the skin when the aerosol composition is sprayed against the skin and left drying. On the other hand, in order to give a uniform emulsion by shaking the aqueous fraction and the oil fraction, it is desirable that the amount of the powder is at least 0.03% by weight, preferably at least 0.05% by weight, more preferably at least 0.1% by weight.

As the effective ingredients to be used in the practice of the present invention, components suitable for the intended applications are chosen. Accordingly, the kinds of the effective ingredients cannot be absolutely determined. Examples of the effective ingredients are, for instance, anti-perspirants, hair tonic effective components, after-shaving lotion effective components, hand lotion effective components, astringent effective components, acne lotion effective components, sun-tan lotion aerosol effective components, body lotion effective components, insect repellents, antipruritic agents, antiinflammatory analgesic agents, fungicides, hair growth effective agents, athlete's foot effective agents, cleansing lotion effective agents, makeup base effective agents, perfume, and the like. The amount of the effective ingredients is adjusted so that the effective ingredients are contained in an amount of 0.01 to 10% by weight, preferably 0.05 to 8% by weight, in particular 0.1 to 6% by weight in the aerosol composition. When the amount of the effective ingredients is less than 0.01% by weight, there is a tendency that the product will not be sufficiently effective for the intended purpose. On the other hand, when the amount exceeds 10% by weight, the effective ingredients will become difficult to disperse.

As mentioned above, an essential component of the concentrate is the effective ingredients, and pentane, an alcohol component, a surface active agent, a powder and the like are added thereto as occasion demands together with water. In addition to the above components, there may be added other components suitable for the intended application, such as polyhydric alcohols, e.g., propylene glycol, ethylene glycol, diethylene glycol, triethylene glycol, glycerin, 1,3-butylene glycol etc.; ketones, e.g., acetone, methyl ethyl ketone, methyl isobutyl ketone, etc.; ethers, e.g., diethyl ether, ethylene glycol monoethyl ether, etc.; esters of fatty acid, e.g., isopropyl myristate, isopropyl palmitate, butyl stearate, hexyl laurate, myristyl myristate, octyldodecyl myristate, etc.; natural animal or plant oils, e.g., jojoba oil, olive oil, avocado oil, etc.; thickners; pigments, etc.

In accordance with the present invention, water is used in the above-mentioned concentrate in order to form a foam which exhibits a crackling sound. As the water, purified water is usually employed. When the alcohol component is employed in the concentrate, the water is used together with the alcohol component in the form of aqueous alcohol solution. On the other hand, when the alcohol component is not employed, the water is solely employed. The amount of water is adjusted so that the water is contained in an amount of 1 to 54% by weight, preferably 2 to 45% by weight, in particular 4 to 36% by weight in the aerosol composition. When the amount of the water is less than 1% by weight, there is a tendency that a formed foam does not exhibit a crackling sound and the dispersibility of the components of the aerosol composition deteriorates. On the other hand, when the amount of the water exceeds 54% by weight, there is a tendency that a formed foam does not exhibit a crackling sound and drying property of the formed foam deteriorates.

While the cracking sound emitted by the foam from an aerosol product is due to the destruction of bubbles upon rapid vaporization of the propellant taken up into the bubbles, the level of this sound is further increased as the foam is crushed by the palms.

The following examples are intended to illustrate the present invention in further detail and should by no means be construed as limiting the scope of the invention. In the Examples, all parts and % are by weight unless otherwise noted.

EXAMPLES 1 TO 16 AND COMPARATIVE EXAMPLES 1 TO 9

Body Cologne Product

A concentrate and a propellant composed of the components shown in Table 1 were mixed together to give an aerosol composition. A pressure-resistant aerosol container having a volume of 300 ml was charged with 120 g of the aerosol composition and was fitted with an aerosol valve and an actuating button to give a body cologne product.

As the physical characteristics of the obtained aerosol composition, the dispersibility, foam deposition, drying property, crackling sound and transparency were investigated by the methods described below. The results are shown in Table 1.

Dispersibility

The aerosol container was shaken 20 times with an amplitude of about 50 cm and the state of dispersion was evaluated against the following criteria.

Criteria:
◯: A uniform emulsion is formed.
×: No uniform dispersion; separation into two phases.

Foam deposition

The aerosol product was sprayed against the arm over an area about 3×3 cm and the dripping property was investigated and assessed against the following criteria.

Criteria:
◯: No dripping
△: Slight dripping
×: Dripping

Cracking sound

The aerosol composition was sprayed against the arm over an area about 3×3 cm and the foam was crushed by hand to assess its crackling sound against the following criteria.

Criteria:
◯: An appreciable cracking sound
△: A faint cracking sound
×: No cracking sound Drying property The aerosol composition was sprayed against the arm over an area about 3×3 cm and the foam was crushed by hand. The crushed foam was allowed to stand for 1 minute and the drying property of the foam on the arm surface was observed and assessed against the following criteria.

Criteria:
◯: Dry feeling to touch
△: Slightly moist feeling to touch
×: Sticky feeling to touch Transparency The aerosol composition was sprayed against the arm and the transparency was observed and assessed against the following criteria.

Criteria:
⊚: Excellent in transparency
◯: Transparent
△: Faint transparent
×: Opaque (milky-white)

TABLE 1

| | | Concentrate (parts) | | | |
| --- | --- | --- | --- | --- | --- |
| | Effective ingredient | Water or aqueous alcohol solution | Surface active agent and/or powder | Other ingredients | Propellant (parts) |
| Ex. No. | | | | | |
| 1 | Perfume 0.5 CH223 | Purified water 29 | PBC-44 0.5 | 13.9 | i-pentane 35 i-butane 35 |
| 2 | Perfume 0.5 CH223 | 20% aqueous ethanol solution 28.2 | PBC-44 0.5 Talc 0.5 | Thickener (methyl cellulose) 0.3 | i-pentane 35 i-butane 35 |
| 3 | Perfume 0.5 CH223 | 30% aqueous ethanol solution 28 | PBC-44 0.5 | Isopropyl myristate 1 | i-pentane 35 i-butane 35 |
| 4 | Perfume 0.5 CH223 | Purified water 9 | PBC-44 0.3 Talc 0.2 | i-pentane 27 | Dichlorotetra- fluoroethane 63 |
| 5 | Perfume 0.5 CH223 | 20% aqueous ethanol solution 26 | NP-10 0.8 Talc 0.7 | Squalane 2 | i-pentane 28 n-butane 42 |
| 6 | Perfume 0.5 CH223 | 25% aqueous ethanol solution 38.5 | NP-20 0.5 | Isopropyl palmitate 0.5 | n-pentane 48 propane 12 |
| 7 | Perfume 0.5 CH223 | 10% aqueous ethanol solution 23.5 | HCO-60 1 | | i-pentane 67.5 Dimethyl ether 7.5 |
| 8 | Perfume 0.5 CH223 | 15% aqueous ethanol solution 16 | PBC-44 0.5 Talc 3 | | n-pentane 40 Dichlorodi- fluoroethane 16 Dichlorotetra- fluoroethane 24 |
| 9 | Perfume 0.5 CH223 | 20% aqueous ethanol solution | PBC-44 1 | jojoba oil 0.1 | i-pentane 45 n-butane 45 |

TABLE 1-continued

| | | | | | | |
|---|---|---|---|---|---|---|
| 10 | Perfume 0.5 CH223 | 15% aqueous ethanol solution 18.95 | NP-20 Zinc dioxide | 8.4 0.05 0.5 | | i-pentane 56 Dichlorotetra- fluoroethane 24 |
| 11 | Perfume 0.5 CH223 | 30% aqueous ethanol solution 21.4 | NP-20 Talc | 0.1 8 | | n-pentane 42 n-butane 28 |
| 12 | Perfume 0.5 CH223 | 15% aqueous ethanol solution 28.95 | PBC-44 | 0.5 | | i-pentane 35 i-butane 35 $N_2$ 0.05 |
| 13 | Perfume 0.5 CH223 | 15% aqueous ethanol solution 28 | NP-20 Talc | 0.2 1.0 | Thickener (methyl cellulose) 0.3 | i-pentane 35 n-butane 35 |
| 14 | Perfume 0.5 CH223 | 5% aqueous ethanol solution 29 | PBC-44 | 0.5 | | i-pentane 35 i-butane 35 |
| 15 | Perfume 0.5 CH223 | 15% aqueous ethanol solution 19.2 28.5 | PBC-44 Talc | 0.5 0.5 | | n-butane 70 |
| 16 | Perfume 0.5 CH223 | 10% aqueous ethanol solution | NP-10 | 0.3 | | n-butane 80 |
| Com. Ex. | | | | | | |
| 1 | Perfume 0.5 CH223 | 70% aqueous ethanol solution 29 | PBC-44 | 0.5 | | i-pentane 35 i-butane 35 |
| 2 | Perfume 0.5 CH223 | 20% aqueous ethanol solution 29.49 | PBC-44 | 0.01 | | i-pentane 35 i-butane 35 |
| 3 | Perfume 0.5 CH223 | 20% aqueous ethanol solution 29.48 | HCO-60 Talc | 0.01 0.01 | | i-pentane 35 i-butane 35 |
| 4 | Perfume 0.5 CH223 | 20% aqueous ethanol solution 22 | PBC-44 | 7.5 | | i-pentane 35 i-butane 35 |
| 5 | Perfume 0.5 CH223 | 20% aqueous ethanol solution 17 | PBC-44 Talc | 0.5 12.0 | | i-pentane 35 i-butane 35 |
| 6 | Perfume 0.5 CH223 | 20% aqueous ethanol solution 17 | PBC-44 Talc | 12.0 0.5 | | i-pentane 35 i-butane 35 |
| 7 | Perfume 11 CH223 | 20% aqueous ethanol solution 18 | PBC-44 Talc | 0.5 0.5 | | i-pentane 35 i-butane 35 |
| 8 | Perfume 0.5 CH223 | 20% aqueous ethanol solution 0.9 | PBC-44 | 0.05 | | i-pentane 94 i-butane 5 |
| 9 | Perfume 1 CH223 | 20% aqueous ethanol solution 68 | PBC-44 | 1 | | i-pentane 8 i-butane 22 |

| | Physical characteristics of aerosol composition | | | | |
|---|---|---|---|---|---|
| | Dispersibility | Foam deposition | Rupture sound | Drying property | Transparency |
| Ex. No. | | | | | |
| 1 | ○ | ○ | ○ | ○ | ⊙ |
| 2 | ○ | ○ | ○ | ○ | ⊙ |
| 3 | ○ | ○ | ○ | ○ | ⊙ |
| 4 | ○ | ○ | ○ | ○ | Δ~○ |
| 5 | ○ | ○ | ○ | ○ | ○ |
| 6 | ○ | ○ | ○ | ○ | ○ |
| 7 | ○ | ○ | ○ | ○ | ⊙ |
| 8 | ○ | ○ | ○ | ○ | Δ~○ |
| 9 | ○ | ○ | ○ | ○ | ⊙ |
| 10 | ○ | ○ | ○ | ○ | ○ |
| 11 | ○ | ○ | ○ | ○ | ○ |
| 12 | ○ | ○ | ○ | ○ | ⊙ |
| 13 | ○ | ○ | ○ | ○ | ○ |
| 14 | ○ | ○ | ○ | ○ | ⊙ |
| 15 | ○ | ○ | ○ | ○ | ○ |
| 16 | ○ | ○ | ○ | ○ | ○ |
| Com. Ex. | | | | | |
| 1 | ○ | X | X | ○ | ○ |
| 2 | X | X | X | Δ | — |
| 3 | X | X | X | Δ | — |
| 4 | ○ | ○ | Δ | X | ○ |
| 5 | ○ | ○ | X | Δ | X |
| 6 | ○ | ○ | Δ | X | X |
| 7 | ○ | Δ | Δ | X | X |
| 8 | X | ○ | Δ | ○ | — |

TABLE 1-continued

| | 9 | ○ | X | X | X | ○ |

(Note)
CH223: produced by Ohzika Perfumery Co., Ltd., trade name; PBC-44: produced by Nikko Chemicals Co., Ltd., trade name; NP-10: produced by Nikko Chemicals Co., Ltd. trade name; Methyl cellulose: produced by Shin-Etsu Chemical Industry Co., Ltd. trade name; HCO-60: produced by Nikko Chemicals Co., Ltd., trade name; NP-20 produced by Nikko Chemicals Co., Ltd., trade name

EXAMPLES 17 TO 22

A concentrate and a propellant composed of the components shown in Table 2 were mixed together to give various kinds of aerosol compositions. A pressure-resistant aerosol composition container having a volume of 300 ml was charged with 120 g of the aerosol composition and was fitted with an aerosol valve and an actuating button to give various kinds of aerosol products.

As the physical characteristics of the obtained aerosol compositions, the dispersibility, foam deposition, foam rupture sound, drying property and transparency were investigated in the same methods as in Examples 1 to 16. The results are shown in Table 2.

TABLE 2

| | | Concentrate (parts) | | | | | |
|---|---|---|---|---|---|---|---|
| Ex. No. | Uses | Effective ingredient | Water or aqueous alcohol solution | Surface active agent and/or powder | | Other ingredients | Propellant (parts) |
| 17 | Antipruritic agent | Methyl salicylate 0.5 l-menthol 0.5 dl-camphor 0.5 Diphenhydramine 0.2 | 15% aqueous ethanol solution 27.3 | PBC-44 Talc | 0.3 0.4 | Thickener (methyl cellulose) 0.3 | i-pentane 35 i-butane 25 n-butane 9 Propane 1 |
| 18 | Insect repellent | Diethyl-toluamide 3 | 30% aqueous ethanol solution 12.7 | NP-20 Talc | 1 3 | Isopropyl myristate 0.3 | i-pentane 40 Dichlorotetra-fluoroethane 40 |
| 19 | Anti-perspirant | Chlorohydroxy aluminum 0.8 | Purified water 15.5 | PBC-44 Talc | 0.5 3 | Isopropyl palmitate 0.2 | i-pentane 32 n-butane 48 |
| 20 | Anti-perspirant | Zinc dioxide 4 Aluminum chlorohydroxy allantoinate 0.5 | 10% aqueous ethanol solution 35 | NP-10 | 0.5 | | i-pentane 42 Dichlorotetra-fluoromethane 15 Dichlorodifluoro-methane 3 |
| 21 | Athlete's foot | Tolnaftate 0.5 l-menthol 0.5 | 20% aqueous ethanol solution 37 | PBC-44 Talc | 0.5 4.0 | Methyl ethyl ketone 7.5 | i-pentane 30 i-butane 20 |
| 22 | After-shave lotion | l-menthol 0.3 | Purified water 16.4 | NP-10 | 0.3 | Glycerine 3 i-pentane 40 | i-butane 10 Dichlorotetra-fluoroethane 30 |

| | Physical characteristics of aerosol composition | | | | |
|---|---|---|---|---|---|
| Ex. No. | Dispersibility | Foam deposition | Rupture sound | Drying property | Transparency |
| 17 | ○ | ○ | ○ | ○ | ○ |
| 18 | ○ | ○ | ○ | ○ | ○ |
| 19 | ○ | ○ | ○ | ○ | ○ |
| 20 | ○ | ○ | ○ | ○ | ○ |
| 21 | ○ | ○ | ○ | ○ | ○ |
| 22 | ○ | ○ | ○ | ○ | ○ |

(Note)
PBC-44: produced by Nikko Chemicals Co., Ltd., trade name
NP-20: produced by Nikko Chemicals Co., Ltd., trade name
NP-10: produced by Nikko Chemicals Co., Ltd., trade name In addition to the ingredients used in the Examples, other ingredients can be used in the Examples as set forth in the specification to obtain substantially the same results.

What we claim is:

1. An aerosol composition comprising: an aqueous solution of a propellant consisting of one or more aliphatic hydrocarbons having a boiling point of −5° to +40° C. in an amount sufficient to propel the composition from an aerosol container; and a surface active agent, wherein the amount of water in the aqueous solution is 1–54% by weight wherein said composition forms a foam exhibiting a crackling sound upon defoaming when subjected to discharge from an aerosol container in the form of a mist or foam.

2. The aerosol composition of claim 1, wherein the aliphatic hydrocarbon is about 5 to about 95% pentane.

3. The aerosol composition of claim 1, wherein the aliphatic hydrocarbon is n-butane.

4. The aerosol composition of claim 1, wherein said propellant comprises pentane and butane.

5. The aerosol composition of claim 1, further comprising an alcohol component selected from the group consisting of ethanol and isopropanol.

* * * * *